United States Patent [19]

Rajoharison

[11] Patent Number: 4,906,757

[45] Date of Patent: Mar. 6, 1990

[54] PROCESS FOR THE PREPARATION OF DEXTROROTATORY 3-(3-PYRIDYL)-1H,3H-PYRROLO [1,2-C]-7-THIAZOLECARBOXYLIC ACID

[75] Inventor: Gerard H. Rajoharison, Villeurbanne, France

[73] Assignee: Rhone-Poulenc Sante, Antony, France

[21] Appl. No.: 213,764

[22] Filed: Jun. 30, 1988

[30] Foreign Application Priority Data

Jul. 2, 1987 [FR] France .................................. 87 09376

[51] Int. Cl.$^4$ .......................................... C07D 513/04
[52] U.S. Cl. .................................................. 546/270
[58] Field of Search ......................................... 546/270

[56] References Cited

FOREIGN PATENT DOCUMENTS 0115979 8/1986 European Pat. Off. .

Primary Examiner—Jane T. Fan
Attorney, Agent, or Firm—Stevens, Davis, Miller & Mosher

[57] ABSTRACT

The acid of formula:

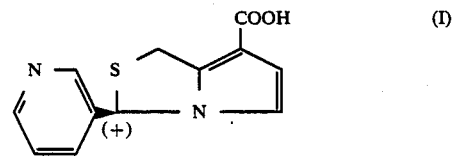

is prepared by reaction of an ester of 2-chloroacrylic acid with an organic salt of 2R, 4R (or predominantly 2R, 4R) 3-formyl-2-(3-pyridyl)-4-thiazolidinecarboxylic acid in the presence of an acid chloride and of triethylamine and then saponifying the ester obtained.

7 Claims, No Drawings

PROCESS FOR THE PREPARATION OF DEXTROROTATORY 3-(3-PYRIDYL)-1H,3H-PYRROLO [1,2-C]-7-THIAZOLECARBOXYLIC ACID

The present invention relates to the preparation of dextrorotatory 3-(3-pyridyl)-1H,3H-pyrrolo-[1,2-c]-7-thiazolecarboxylic acid of the formula:

(I)

which can be used as an intermediate for the preparation of drugs for treating disorders involving the physiological role of the PAF-acether, particularly for treating allergies, inflammation and for preventing the aggregation of blood platelets. Such products are known from European Pat. No. 0,115,979.

Until now, the acid of the formula (I) has been prepared from the corresponding racemic acid by resolution using an optically active base such as(+)α-methylbenzylamine [(+)α-MBA], that is to say by conventional methods. Racemic 3-(3-pyridyl)-1H,3H-pyrrolo-[1,2-c]-7-thiazolecarboxylic acid has been prepared from 3-formyl-2-(3-pyridyl)-4-thiazolidinecarboxylic acid by the process described in European Pat. No. 0,115,979 according to the following reaction scheme:

mixture of cis and trans compounds
(II)

mixture of dextrorotatory and laevorotatory products
(III)

(IV) Racemic product

This synthesis has three main disadvantages:

(1) whatever the proportions of the cis and transforms of the formulated compound of formula (II), the yield of nitrile of formula (III) is never higher than 36%;

(2) the condensation of chloroacrylonitrile with the acid of formula (II) requires 5 equivalents of chloroacrylonitrile per mole of acid, and this entails the need to recover and recycle the chloroacrylonitrile when the process is operated on an industrial scale, and (3) whatever the proportions of the dextrorotatory and laevorotatory forms of the nitrile of formula (III), the severe saponification conditions required to produce the acid of formula (IV) result in a racemic acid being obtained, and this necessarily requires a subsequent separation by resolution using an optically active base which entails numerous recrystallizations and a drop in yields.

Consequently, the whole synthesis does not make it possible to prepare the acid of formula (I) in a yield of more than approximately 10% from the formylated acid of the formula (II).

The present invention provides a new process which reduces or eliminates these disadvantages. The new process introduces the following basic modifications into the above synthesis:

use of 3-formyl-2-(3-pyridyl)-4-thiazolidinecarboxylic acid of 2R,4R or predominantly 2R,4R form;

replacement of chloroacrylonitrile by an ester of 2-chloroacrylic acid, thus leading to the production of an ester which can easily be saponified under nonracemizing conditions; and replacement of acetic anhydride by an acid chloride in the condensation reaction with the formylated acid and use of a solvent of low boiling point which permits the reactions to be performed under mild conditions, and avoids tar formation.

Thus, the process of the present invention for the preparation of the detrorotatory acid of formula I comprises reacting an ester of 2-chloroacrylic acid of the formula:

$$CH_2=C-COOR \quad (V)$$
$$\phantom{CH_2=}|$$
$$\phantom{CH_2=}Cl$$

in which R denotes alkyl of 1 to 4 carbon atoms in a straight or branched chain, benzyl or aryl, with an organic base salt of (2R,4R)-3-formyl-2-(3-pyridyl)-4-thiazolidinecarboxylic acid of the formula:

(VI)

in the presence of an acid chloride and of triethylamine to produce an ester of the general formula:

(VII)

in which R is as hereinbefore defined and saponifying the ester of the formula (VII) under nonracemizing conditions.

It is particularly advantageous to employ, as the acid chloride, para-toluenesulphonyl chloride, methanesulphonyl chloride or oxalyl chloride, to obtain the dextrorotatory ester of formula VII.

In practice, the reaction is generally carried out in a chlorinated organic solvent capable of dissolving the salt of the acid of formula (VI)), such as dichloromethane or dichloroethane at a temperature of between 20° C. and the reflux temperature of the reaction mixture.

A trialkylamine such as triethylamine, tributylamine or pyridine may be employed as an organic base to form the salt of the acid of formula (VI).

According to a feature of the invention, the ester of 2-chloroacrylic acid of the general formula (V) is prepared, without being isolated, by the action of an organic base on the corresponding ester of 1,2-dichloropropionic acid of the general formula:

(VIII)

in which R is as hereinbefore defined. The organic base employed is generally the base which is used to form the salt of the acid of formula (VI), as already stated, preferably triethylamine. The reaction is generally carried out in an organic solvent such as that used for the condensation of the ester of formula (V) with the acid of formula (VI), preferably dichloromethane or 1,2-dichloroethane.

The saponification of the ester of the formula (VII) may be carried out by any method known to the person skilled in the art and capable of converting an ester into acid under mild, nonracemizing conditions. It is particularly advantageous to perform the saponification by the action of an alkali metal hydroxide such as sodium hydroxide or potassium hydroxide in an aqueous alcoholic mixture at a temperature of between 25 and 45° C.

The acid of the formula (VI) may be prepared by the method described in European Pat. No. 0,115,979, followed by a recrystallization to obtain the acid of 2R, 4R form.

The acid of the formula (I), and the synthesis intermediates, may be purified by the usual means known to the person skilled in the art, for example by chromatography, recrystallization or distillation.

Cycloaddition reactions leading to optically active pyrrolothiazoles are already known [H. T. Nagajawa, D. J. W. Goon and F. N. Shirdta, J. Heterocyclic Chem., 18, 1047 (1981)]. The reactions described in this publication have been performed on different substrates and using different conditions (use of acetic anhydride and heating to 100°-105° C.). The esters of 2-chloroacrylic acid (particularly ethyl 2-chloroacrylate) had never been employed for the preparation of pyrrolothiazoles. It was not obvious, therefore, that they would lead to the acid of the formula (I) in a stereoselective manner. Furthermore, adaptation of the conditions used by Nagasawa et al., referred to above in the case of ethyl 2-chloroacrylate and of 3-formyl-2-(3-pyridyl)-4-thiazolidinecarboxylic acid leads to low yields [of the order of 20% starting from the acid of the formula (VI)]. The poorness of the yields is due chiefly to the significant tar formation.

Thus, the present invention unexpectedly provides a solution to the problem investigated, namely the preparation of the acid of formula (I) in improved yields, without the need for a separation of diastereoisomers.

The following examples show in greater detail how the invention may be employed in practice.

EXAMPLE 1

(a) Preparation of the ester (formula (VII) with R=C₂H₅) in the presence of tosyl chloride.

Tosyl chloride (8,169 g), dichloromethane (16.5 liters) and ethyl 2,3-dichloropropionate (7,781 g) are charged into a 100-liter reactor. This mixture is heated to reflux (40°-42° C.) and a solution, prepared beforehand, of the 2R, 4R diastereoisomer of 3-formyl-2-(3-pyridyl)-4-thiazolidinecarboxylic acid (9,350 g) in dichloromethane (13.8 liters) and triethylamine (4,375 g) is then added over 1 hour 45 minutes. After 20 minutes' additional stirring, triethylamine (13,126 g) is added over 1 hour and 15 minutes. The stirring is continued under reflux (40°-42° C.) for one and a half hours. The reaction mixture is cooled to 20° C. and the reaction mixture is then taken up with distilled water (12 liters). The organic phase is separated off, and is washed 3 times with distilled water (20 ° C. liters in all) and is then dried over sodium sulphate (6 kg). After filtration and evaporation of the solvent, a crude mixture (14,030 g) is obtained, containing ethyl 3-(3-pyridyl)-1H,3H-pyrrolo[1,2-c]-7-thiazolecarboxylate (8,135 g; HPLC determination, 58% concentration) (yield =75.6% base on the thiazolidine used).

The enantiomeric purity of the product obtained is higher than 99.4% of the d enantiomer by HPLC analysis on a chiral Pirkle type 1-A column (hexane/isopropanol eluent: 90/10, flow rate 0.3 ml/min, P =4 bars).

(b) Preparation of the acid of the formula (I)

The crude ester (84.35 g) obtained above is dissolved in ethanol (134 cc) and a solution containing potassium hydroxide pellets (35.3 g) and water (214 cc) is added at 25° C. over 20 minutes. The mixture is heated to 40° C. and this temperature is maintained for 18 hours.

Decolorizing charcoal (8.34 g)is then added and heating is continued at 40° C. for another 2 hours. A hot filtration is carried out in the presence of diatomaceous earth. After cooling to 20° C., the filtrate is adjusted to pH 4 by the addition of concentrated hydrochloric acid (40 cc). The crystals which have appeared are separated off by filtration and are then washed three times with water and dried under reduced pressure (20 mm of mercury; 2.7 kPa) at 20° C. In this manner, 3-(3-pyridyl)-1H,3H-pyrrolo[1,2-c]-7-thiazolecarboxylic acid (41.9 g; 93% purity; 95.3% yield) is obtained in the form of ochrecoloured crystals melting at 214° C. and exhibiting a rotatory power= +151° (c=2, N NaOH). The overall yield is then 72% relative to the 3-formyl-2-(3-pyridyl)-4-thiazolidinecarboxylic acid employed.

The 1H NMR analysis in the presence of 1(−)α-methylbenzylamine permits only the salt of the d enantiomer of the acid described (enantiomeric purity >95%) to be observed.

EXAMPLE 2

(a) Preparation of the ester (formula (VII) with R=C₂H₅) in the presence of tosyl chloride para-Toluenesulphonyl chloride (9,562 g), dichloromethane (20 liters) and ethyl 2,3-dichloropropionate (9,108 g, 95% purity) are charged into a 100-liter reactor. The mixture is heated until the dichloromethane refluxes (40° C.) and then a preformed mixture of 2R,4R-3-formyl-2-(3-pyridyl)-4-thiazolidinecarboxylic acid 10,990 g, of triethylamine (5,120 g) and of dichloromethane (16.2 liters) is then added over 1 hour at this temperature. Stirring is continued for another 15 minutes, and triethylamine (21.336 liters) is then added over one and a half hours at the reflux temperature of dichloromethane. The reaction is prolonged for another hour at this temperature. After cooling to ambient temperature, the reaction mixture is taken up with water (15 liters), the organic phase is separated off and the aqueous phase is extracted with dichlorormethane (2×6 liters). The organic extracts are combined and are then washed 3 times with water (24 liters in all). After evaporation of the solvent, a brown oil (15,028 g), which crystallizes on standing, is obtained. The HPLC analysis of this product permits ethyl 3-(3-pyridyl)-1H,3Hpyrrolo[1,2-c]thiazolecarboxylate (10,670 g) to be determined, i.e. an 84.6% yield based on the acid employed.

(b) Purification of the ester obtained

The crude ester (114 g) obtained earlier is dissolved in ethanol (470 cc). The mixture is heated to reflux and decolorizing charcoal (10 g) is then added. The materials are left stirred under reflux for one and a half hours. After cooling to ambient temperature, they are filtered through diatomaceous earth. The solvent is evaporated off and the residue is treated with silica (275 g; 0.063–0.2 mm) in the presence of dichloromethane (600 cc). After evaporation of the solvent, the residue is stirred in the presence of pentane (100 cc). The product precipitates out. In this manner, ethyl 3-(3-pyridyl)7H,3H-pyrrolo[1,2-c]thiazolecarboxylate (69.3 g) is obtained in the form of a light-yellow coloured powder melting at 64° C. (HPLC purity=95.5%).

(c) Preparation of the acid of the formula (I)

A solution of potassium hydroxide (29 g) in distilled water (175 cc) is added over 10 minutes to a solution of the ester (40 g) purified earlier, in ethanol (110 cc). The mixture is heated to 40° C. for 17 hours and decolorizing charcoal (4 g) is then added. After another 2 hours' heating at 40° C., the mixture is cooled to 20° C. and is then filtered through diatomaceous earth. This mixture is brought to pH 4 by adding concentrated (37%) hydrochloric acid (30 cc). The crystals which have appeared are separated off by filtration, are washed three times with water and are then dried under reduced pressure (20 mm of mercury; 2.7 kPa) at 20° C. In this manner 3-(3-pyridyl)-1H,3H-pyrrolo[1,2-c]-7-thiazolecarboxylic acid (31.4 g) is obtained in the form of cream-coloured crystals melting at 215° C. 1H NMR analysis of the product obtained in the presence of 1(-)α-methylbenzylamine allows only the salt of the d enantiomer of the acid described (enantiomeric purity >95%) to be observed. The reaction yield is 88% based on the ester employed, i.e. a 63.3% overall yield based on 3-formyl-4-thiazolidinecarboxylic acid.

EXAMPLE 3

(a) Preparation of the ester (formula (VII) with R=C₂H₅) 5) in the presence of methanesulphonyl chloride A solution containing the 2R,4R diastereoisomer of 3-formyl-2-(3-pyridyl)-4-thiazolidinecarboxylic acid (10 g), triethylamine (6.45 cc) and dichloromethane (38.5 cc) is added over one hour to a stirred solution of methanesulphonyl chloride (3.54 cc) in dichloromethane (47 cc) at a temperature in the region of 20° C. Stirring is left to continue for 15 minutes and a solution containing ethyl 2-chloroacrylate (6.21 g), triethylamine (13 cc) and dichloromethane (21 cc) is then added over 35 minutes at 20° C. Stirring is allowed to continue for 30 minutes and the mixture is then refluxed (40° C.) for 30 minutes. The mixture is then cooled to 20° C. and the reaction mixture is taken up with distilled water (100 cc). The aqueous phase is extracted with dichloromethane (25 cc) and the organic layer is washed with a half-saturated aqueous solution of sodium chloride. After drying with sodium sulphate, filtering and evaporation of the solvent, a crude product (10.75 g) is obtained. This is purified by liquid chromatography on a 50-mm diameter column containing silica (100 g; 0.063–0.2 mm), eluting with ethyl acetate. In this manner, pure ethyl 3-(3-pyridyl)-1H,3H-pyrrolo[1,2-c]-7-thiazolecarboxylate (7 g) is obtained in the form of a yellow oil which crystallizes on standing (60.8% yield based on the acid employed).

(b) Preparation of the acid of the formula (I)

A solution containing potassium hydroxide (4.43 g) and distilled water (27 cc) is added over 10 minutes to a solution of the ester obtained earlier (6.13 g), in ethanol (17 cc). The mixture is heated to 40° C. for 18 hours and decolorizing charcoal (0.617 g) is then added. After an additional 1 hour at 40° C., the mixture is cooled to 20° C. and is then filtered. The mixture is brought to pH 4 by adding concentrated hydrochloric acid. The crystals which have appeared are separated off by filtration and are then washed three times with water and are dried under reduced pressure (20 mm of mercury; 2.7 kPa) at 20° C. In this manner, 3-(3-pyridyl)-1H,3H-pyrrolo[1,2-c]-7-thiazolecarboxylic acid (4.55 g) is obtained in the form of cream-coloured crystals melting at 214° C. and exhibiting a rotatory power = +158° (c =2; N NaOH), i.e. a 50.3% overall yield based on the 3-formyl-2-(pyridyl)-4-thiazolidinecarboxylic acid employed.

EXAMPLE 4

(a) Preparation of the ester (formula VII with R=C₂H₅) in the presence of oxalyl chloride The 2R,4R diastereoisomer of 3-formyl-2-(3-pyridyl)-4-thiazolidinecarboxylic acid (10 g) and dichloromethane (63.5 cc) are charged into a 250-cc four-necked flask fitted with a mechanical stirrer, a dropping funnel, a thermometer and a condenser connected to a gasometer. Triethylamine (6.45 cc) is then added dropwise over 14 minutes at ambient temperature. The mixture becomes homogeneous after 10 minutes' stirring. A solution of oxalyl chloride (5.90 g) in dichloromethane (22 cc) is then added over 48 minutes' at 24° C. During the addition, the mixture progressively becomes heterogeneous, orange-yellow in colour, with a gaseous release of carbon monoxide and carbon dioxide. Stirring is allowed to continue for another 15 minutes at ambient temperature and a solution containing ethyl 2-chloroacrylate (6.20 g), triethylamine (9.44 g) and dichloromethane (21 cc) is then added over 34 minutes. A release of carbon dioxide is observed again; the mixture progressively becomes homogeneous and chestnut-brown in colour. The reaction mixture is then heated to 40° C. for 30 minutes. The mixture is cooled to 20° C. and is taken up with water (100 cc). The organic phase is separated off and the aqueous phase is then extracted with dichloromethane (100 cc) and the organic extracts are dried over sodium sulphate. After evaporating the solvent under reduced pressure (20 mm of mercury; 2.7 kPa) at 20° C., a crude product (11 g) is obtained. This is purified by liquid chromatography on a 50-mm diameter column containing silica (100 g; 0.063–0.2 mm), eluting with ethyl acetate. In this manner, pure ethyl 3-(3-pyridyl)-1H,3H-pyrrolo[1,2-c]-7-thiazolecarboxylate (5.78 g) is obtained in the form of a yellow oil which crystallizes on standing (50.2% yield based on the acid employed).

(b) Preparation of the acid of formula (I)

A solution containing potassium hydroxide (3.8 g) and distilled water (25 cc) is added over 10 minutes to a solution of the ester obtained earlier (5.26 g), in ethanol (14.6 cc). The mixture is heated to 40° C. for 18 hours. Decolorizing charcoal (0.526 g) is then added. After an hour of additional heating at 40° C., the mixture is cooled to 20° C. and is then filtered. The mixture is then brought to pH 4 by adding concentrated hydrochloric acid. The crystals which have appeared are separated off by filtration, and are then washed three times with water and are dried under reduced pressure (20 mm of mercury, 2.7 kPa) at 20° C. In this manner, 3-(3-pyridyl)-1H,3H-pyrrolo[1,2-c]-7-thiazolecarboxylic acid (4.32 g) is obtained in the form of cream-coloured crystals melting at 215° C. and exhibiting a rotatory power= +159.7° (c=2, N NaOH), i.e. a 45.9% overall yield based on the 3-formyl-2-(3-pyridyl)-4-thiazolidinecarboxylic acid employed.

I claim:

1. A process for the preparation of dextrorotatory 3-(3-pyridel)-1H,3H-pyrrolo[1,2-c]-7-thiazolecarboxylic acid of the formula:

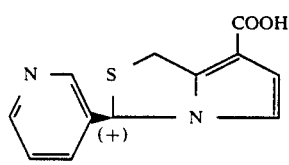

(I)

which comprises reacting an ester of 2-chloroacrylic acid of formula:

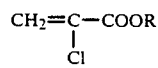

(V)

in which R denotes alkyl of 1 to 4 carbon atoms in a straight or branched chain, benzyl, or aryl, with an organic salt of 2R,4R 3-formyl-2-(3-pyridyl)-4-thiazolidinecarboxylic acid of the formula:

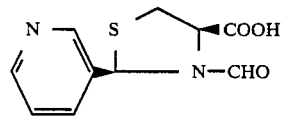

(VI)

in the presence of an acid chloride and of triethylamine to produce an ester of the formula:

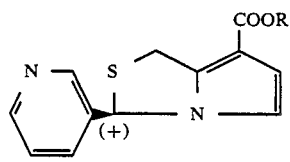

(VII)

in which R is as hereinbefore defined, and saponifying the ester of formula (VII) under nonracemizing conditions.

2. Process according to claim 1, wherein the acid chloride employed is para-toluenesulphonyl chloride, methanesulphonyl chloride, or oxalyl chloride.

3. Process according to claim 1, wherein the base employed in the organic salt of the acid of formula (VI) is triethylamine.

4. Process according to claim 1, wherein R is ethyl.

5. Process according to claim 1 wherein the saponification of the ester of formula (VII) is performed with an aqueous alcoholic solution of potassium hydroxide at 25° to 45° C.

6. Process according to claim 1, wherein the ester of 2-chloroacrylic acid of formula (V) is prepared in situ by the action of a base on an ester of 2,3-dichloropropionic acid of the formula:

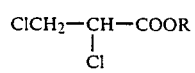

(VIII)

in which R as defined in claim 1.

7. Process according to claim 6, wherein the base employed to prepare the ester of 2-chloroacrylic acid is triethylamine.

* * * * *